US009681997B2

(12) United States Patent
Sheehan

(10) Patent No.: US 9,681,997 B2
(45) Date of Patent: Jun. 20, 2017

(54) DUAL-FUNCTION FASTENING MEMBER FOLD CONFIGURATION FOR DISPOSABLE DIAPERS

(71) Applicant: The Procter & Gamble Company, Cincinnati, OH (US)

(72) Inventor: Astrid Annette Sheehan, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 368 days.

(21) Appl. No.: 14/074,923

(22) Filed: Nov. 8, 2013

(65) Prior Publication Data

US 2015/0133885 A1    May 14, 2015

(51) Int. Cl.
| | |
|---|---|
| A61F 13/15 | (2006.01) |
| A61F 13/49 | (2006.01) |
| A61F 13/494 | (2006.01) |
| A61F 13/62 | (2006.01) |
| A61F 13/56 | (2006.01) |
| A61F 13/58 | (2006.01) |
| A61F 13/551 | (2006.01) |

(52) U.S. Cl.
CPC ...... *A61F 13/49001* (2013.01); *A61F 13/494* (2013.01); *A61F 13/5633* (2013.01); *A61F 13/58* (2013.01); *A61F 13/15747* (2013.01); *A61F 13/4942* (2013.01); *A61F 13/49413* (2013.01); *A61F 13/55115* (2013.01); *A61F 13/5622* (2013.01); *A61F 13/581* (2013.01); *A61F 13/62* (2013.01); *A61F 13/622* (2013.01); *A61F 2013/5677* (2013.01); *A61F 2013/5694* (2013.01)

(58) Field of Classification Search
CPC .... A61F 13/5622; A61F 13/62; A61F 13/622; A61F 13/581; A61F 13/58; A61F 2013/5694; A61F 2013/5677
USPC ... 604/385.03, 386, 387, 389, 390, 394, 396
See application file for complete search history.

(56) References Cited

U.S. PATENT DOCUMENTS 4,869,724 A * 9/1989 Scripps ................. A61F 13/581
604/389
5,156,793 A   10/1992 Buell et al.
5,167,897 A   12/1992 Weber et al.
(Continued)

FOREIGN PATENT DOCUMENTS

CA    2 787 113 A1    6/2007
GB      1441567 A      7/1976

OTHER PUBLICATIONS

PCT International Search Report, mailed Mar. 5, 2015 (12 pages).
U.S. Appl. No. 13/538,140, filed Jun. 29, 2012, Arman Ashraf.

*Primary Examiner* — Jacqueline Stephens
(74) *Attorney, Agent, or Firm* — William E. Gallagher

(57) ABSTRACT

A disposable diaper having fastening members with an advantageous folding configuration is disclosed. The fastening members may be imparted with two longitudinal folds to create a z-fold configuration that serves dual functions of consolidating the fastening members for purposes of protecting them in manufacturing and packaging processes downstream of the point at which the fastening members are included on the diaper, and providing the consumer with easy access and manipulability of the fastening member at the time the diaper is to be applied to a baby.

3 Claims, 7 Drawing Sheets

(56) References Cited

U.S. PATENT DOCUMENTS

| | | | |
|---|---|---|---|
| 6,524,294 B1* | 2/2003 | Hilston | A61F 13/62 604/386 |
| 7,455,665 B2 | 11/2008 | Wendelstorf et al. | |
| 7,527,617 B2 | 5/2009 | Shimaida et al. | |
| 7,799,162 B2 | 9/2010 | Wood et al. | |
| 7,862,549 B2 | 1/2011 | Desai et al. | |
| 8,177,766 B2 | 5/2012 | Mansfield | |
| 8,227,071 B2 | 7/2012 | Wood et al. | |
| 2004/0138639 A1 | 7/2004 | Ito et al. | |
| 2004/0181200 A1 | 9/2004 | Desai et al. | |
| 2011/0092947 A1 | 4/2011 | Kline et al. | |
| 2012/0065607 A1* | 3/2012 | Konig | A61F 13/5633 604/385.201 |
| 2013/0138073 A1 | 5/2013 | Horn et al. | |

* cited by examiner

DUAL-FUNCTION FASTENING MEMBER FOLD CONFIGURATION FOR DISPOSABLE DIAPERS

FIELD OF THE INVENTION

Many currently marketed disposable diapers include a pair of oppositely-disposed fastening members extending laterally outward from the main chassis portion of the diaper at the rear waist region. Such fastening members typically end with distal fastening strip, tape or similar member bearing a fastener of some type thereon, configured to engage a front portion of the diaper chassis; such front portion is sometimes called the "landing zone." When the diaper is stretched out and appropriately placed beneath a reclining baby with wearer-facing surfaces up, each fastening member may be pulled laterally outward from the chassis, wrapped about one of the baby's hips, and fastened to the front portion of the diaper at the landing zone, via the fastener, thereby fastening the diaper about the baby.

Many disposable diapers are currently manufactured in a processing line such that the longitudinal axes of the diaper components and completed diaper chasses are parallel with the machine direction of the line. Fastening members may be included or attached to the sides of the diaper chasses at various stages during the manufacture. After attachment, the fastening members typically extend laterally outwardly of the chasses, i.e., in the cross direction. Regardless of the particular stage at which the fastening members may be included or attached, it is often desired that they be controlled in some manner in downstream processing, because if left uncontrolled, they may be free to flap about as they move through the line, which may create risk of problems in processing and quality control. For example, uncontrolled fastening members could in some circumstances be torn off in downstream processes. Accordingly, in many manufacturing lines folding equipment may be situated downstream of the location at which fastening members are included or attached. Such folding equipment is typically configured to fold the fastening members laterally inwardly, over the wearing-facing sides of the diaper chasses.

While such techniques may be effective for controlling the fastening members for purposes of downstream processing, it can result in fastening members that are inconsistently folded, bunched toward the middle and/or are generally inconvenient or annoying for the caregiver/consumer to access, grasp and stretch out when the caregiver opens the diaper and applies it to a baby. Consequently, there is room for improvement in the manner in which fastening members are folded for control purposes.

DETAILED DESCRIPTION OF THE INVENTION

Figure 1:
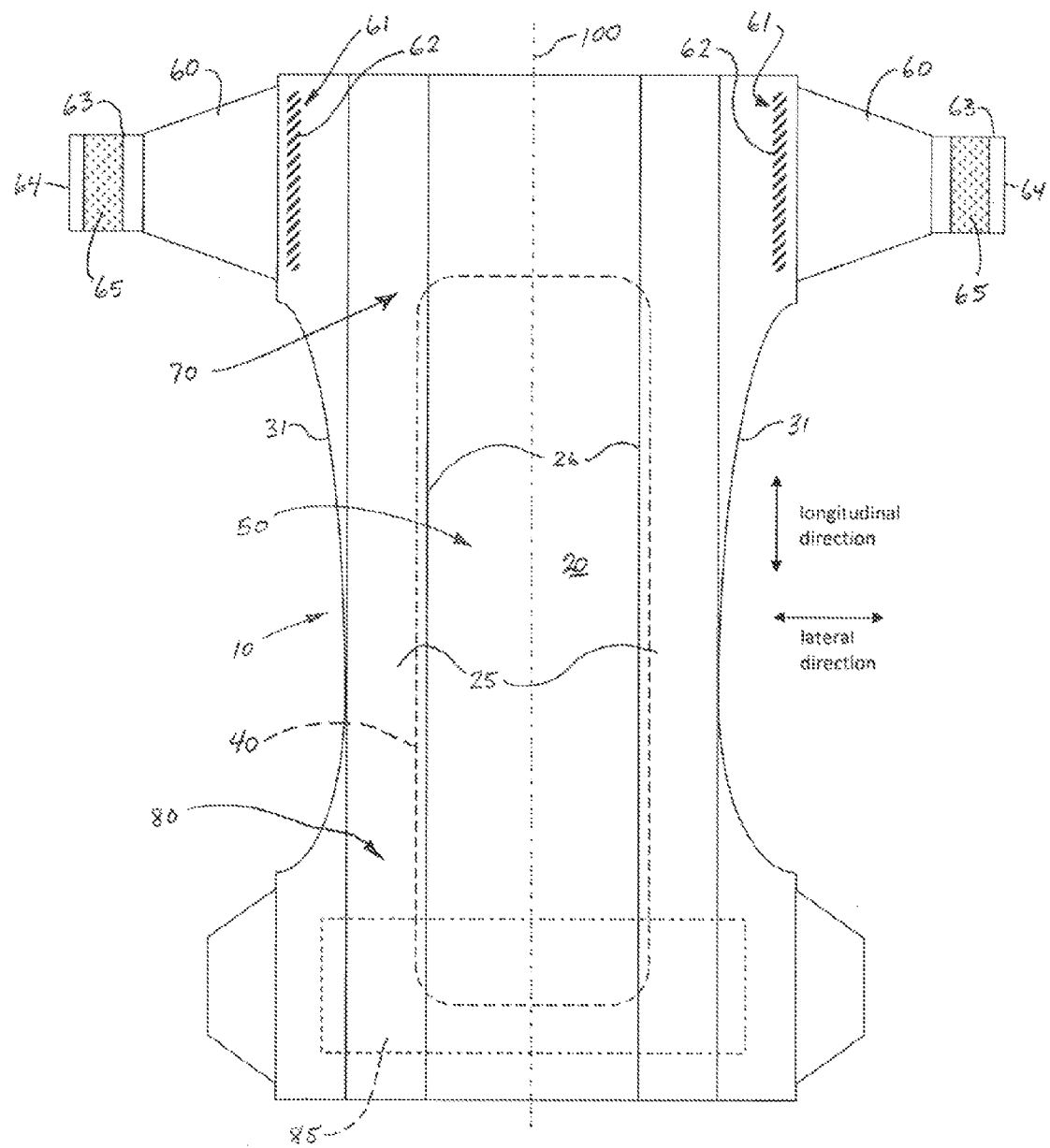
FIG. 1 is a plan view of a disposable diaper shown extended longitudinally and laterally against any contraction induced by included elastic members, with wearer-facing surfaces up.

Herein, "longitudinal" with respect to a disposable diaper refers to a direction generally perpendicular to the waist edges of the diaper; and "lateral" refers to a direction generally parallel to the waist edges of the diaper.

The present invention relates to disposable diapers having fastening members. Referring to all figures, a disposable diaper of the type contemplated herein may have a chassis 10 formed of a liquid permeable topsheet 20 forming a wearer-facing side, a liquid impermeable backsheet 30 forming an outward-facing side, and an absorbent core 40 disposed therebetween. A pair of barrier cuffs 25 may be disposed on the wearer-facing side, and may have proximal edges affixed thereto by any suitable mechanism. Free distal edges 26 of barrier cuffs 25 may have longitudinally-oriented elastic strands, strips or other cuff elastic members (not shown) disposed therealong, to cause the cuffs to gather longitudinally along their free edges 26 and provide a gasketing barrier structure through the crotch region 50. The elastic members may be disposed in the barrier cuff structures in a longitudinally pre-strained condition. The leg edges 31 may be formed of the longitudinal edges of any of the backsheet 30, topsheet 20, proximal portions of barrier cuffs 25, or a layered combination of any of these. Leg edges 31 may be cut and contoured as shown, or may be straight. Leg edges 31 also may have longitudinally-oriented elastic strands, strips or other leg elastic members (not shown) disposed therealong, to cause the leg edges to gather about the wearer's legs. For example, leg elastic members may be sandwiched between the topsheet 20 and the backsheet 30, or between the material forming the barrier cuffs 25 and the backsheet 30, or between the material forming the barrier cuffs 25 and the topsheet 20, proximate to the leg edges. The leg elastic members may be disposed along the leg edges in a longitudinally pre-strained condition.

A disposable diaper of the type contemplated herein may include a pair of fastening members 60, extending laterally away from the longitudinal axis 100 of the diaper in the rear region 70. Fastening members 60 may be formed of continuous lateral extensions of the material forming backsheet 30 and/or topsheet 20, or, as suggested in the figures, may each be formed of a separate piece of material that is affixed to the chassis 10, for example, to the topsheet 20 and/or the backsheet 30, at attachment locations 61 via thermal bonds, adhesive or any other suitable attachment mechanism 62. Fastening members 60 may be affixed to the outward-facing side of the backsheet 30, or to the wearer-facing side of the topsheet 20, or to a wearer-facing side of material forming the barrier cuffs 25. Alternatively, fastening members 60 may be sandwiched and affixed between the topsheet 20 and the backsheet 30.

In a non-limiting example, fastening members 60 may be formed of a stretch laminate material configured to impart elastic stretch and contraction in the lateral direction, enhancing comfort and fit of the diaper about the baby. For purposes herein, "stretch laminate" means an extensible and elastic web material comprising a combination including an elastic polymeric material (such as a film, or laterally-oriented strips or strands formed of elastomeric polymer) layered, laminated or interspersed with one or more layers of nonwoven material. In one example a stretch laminate may be formed of a laminate of an elastomeric film sandwiched between two layers of nonwoven. Suitable stretch laminate materials are described in, for example, PCT Application No. WO 2005/110731, and U.S. Application Publication Nos. US 2011/0092947; US 2007/0293111; US 2004/0181200 and US 2004/0193133, which are incorporated herein fully by reference to the extent not inconsistent herewith. A suitable stretch laminate may be activated by mono-axial stretching of the section of the laminate which contains the laminated-in elastomeric material, in a manner described in more detail, for example, in U.S. Pat. No. 4,834,741, and in published PCT Applications Nos. WO 1992/015446 and WO 1992/015444, which are incorporated herein fully by reference to the extent not inconsistent herewith.

Each of fastening members 60 may terminate in a section of tape, strip or other suitable graspable end member 63 having a distal end 64. Graspable end member 63 also may simply be formed of an extension(s) of the material(s) forming fastening member 60. End member 63 may have a fastener 65 disposed thereon proximate to distal end 64, attached thereto by adhesive, thermal bonding or any other suitable attachment mechanism. Fastener 65 may be any suitable type of fastener mechanism configured to fastenably engage with landing zone 85 disposed on the outside of the chassis in the front region 80. In a non-limiting example, fastener 65 may be a patch of hooks and landing zone 85 may be formed of a patch of loops material, in a hook-and-loop fastening system as is often used in current disposable diapers. In a non-limiting example, landing zone 85 may be formed of a nonwoven web material formed of bicomponent or multicomponent fibers such as, for example, described in U.S. Patent Application Publication No. US 2013/0138073, and U.S. patent application Ser. No. 13/538,140, which are incorporated fully herein by reference to the extent not inconsistent herewith. In another non-limiting example, a patch of hooks may be configured to fastenably engage a nonwoven web material forming the outer layer of the backsheet 30 without the need for an added patch of loops material.

Figure 2:
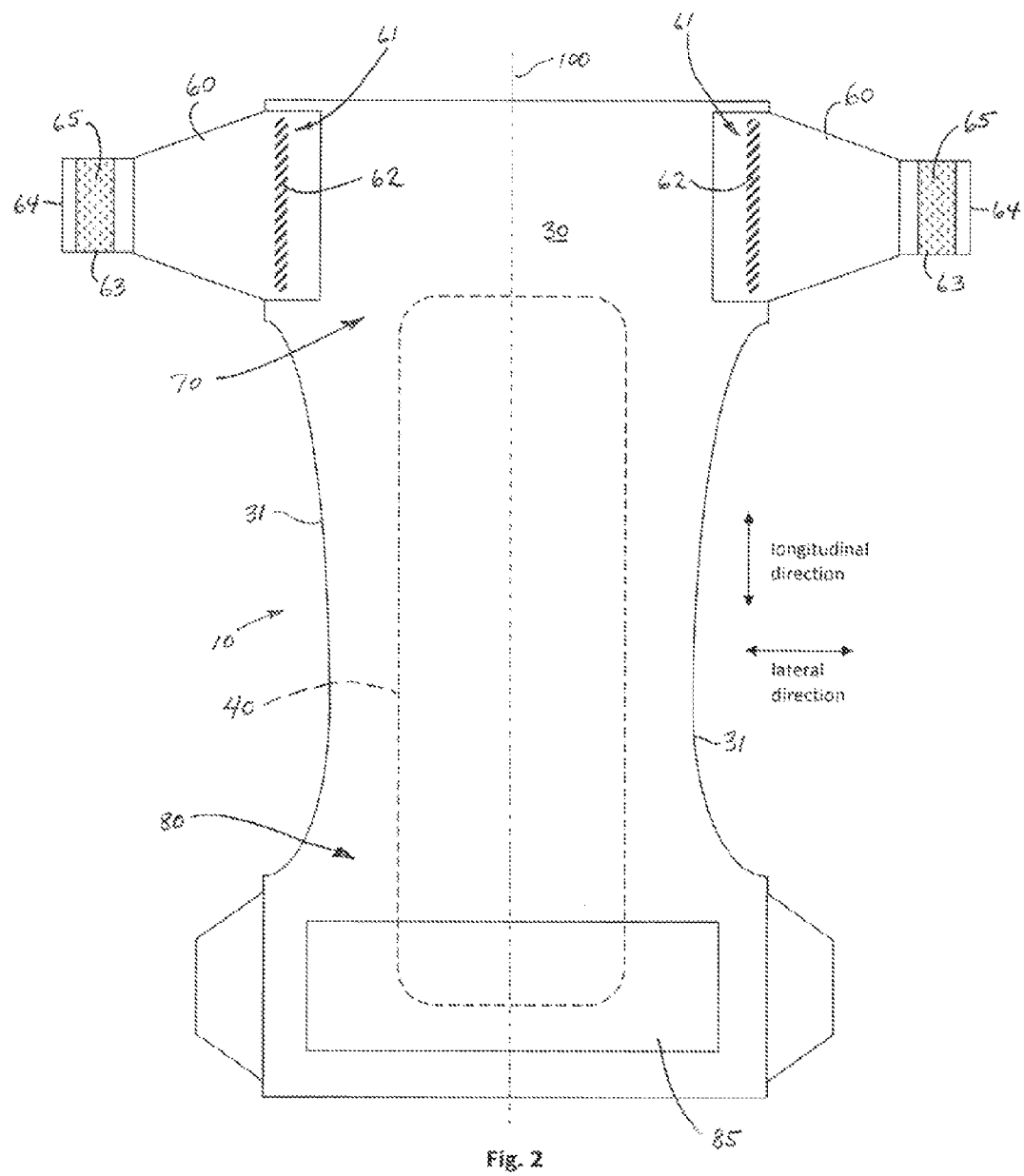
FIG. 2 is a plan view of a disposable diaper shown extended longitudinally and laterally against any contraction induced by included elastic members, with outward facing surfaces up.

In manufacturing lines for many types of currently marketed disposable diapers, the products are constructed along the machine direction of the line such that the longitudinal axis 100 of the finished diaper product is parallel with the machine direction. Considering FIGS. 1 and 2, it will be appreciated that fastening members 60 may be subject to uncontrolled flapping as they are moved through the line, because only the central portions of the chassis components may be gripped by conveying/processing mechanisms as the components are moved through the line. If the fastening members 60 are allowed to extend laterally and flap about, they may be exposed to being inconsistently crumpled when packaged (which may cause consumer impressions of poor quality), or even torn off or damaged, or may obstruct processing operations in some circumstances. Accordingly, folding equipment may be included to impart temporary folds to the fastening members 60 to dispose them laterally inwardly of their extended lengths (i.e., toward the longitudinal axis 100) to keep them under control during processing downstream of the point at which they were added.

In connection with a diaper design including other new features, various types of fastening member temporary folding configurations have been considered and tested with consumers. From such testing it is believed that a configuration having features reflected in FIGS. 3-6 provides for substantially reduced caregiver effort as compared with other possible configurations, because the tasks of locating a graspable end member 63, grasping it, extending the fastening member, wrapping the fastening member about the baby's hip, and fastening it to the landing zone, can be performed with one hand in a simple easy motion. For this reason it is believed that a configuration having such features will be preferred by consumers/caregivers over other configurations.

Referring to FIGS. 3-5A, each fastening member 60 may be imparted with a first longitudinal fold 90, at which the fastening member 60 is folded over itself, toward the outside in the z-direction (i.e., over the outward-facing surface of the diaper). Each fastening member 60 may be imparted with a second longitudinal fold 91 at which the fastening member 60 is again folded over itself, again toward the outside in the z-direction. The two longitudinal folds 90, 91 give the fastening member a "z" fold configuration when viewed in lateral cross section; see FIG. 5A. It can be appreciated from the figures that the lateral length of each fastening member is thereby gathered laterally inward (toward the longitudinal axis), providing for control of the fastening members in processing.

Figure 5A:
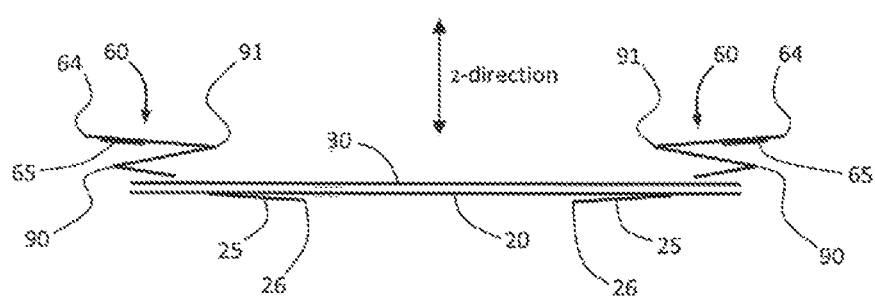
FIG. 5A is a schematic, exploded cross section of the diaper of FIG. 3, taken along line 5-5 in FIG. 3.
Figure 5B:
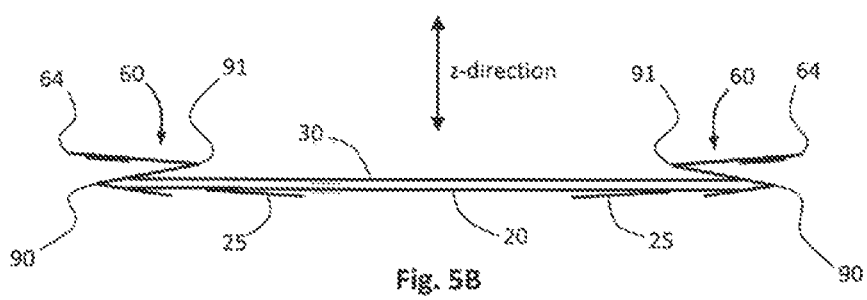
FIG. 5B-5D are schematic, exploded cross sections of diapers having alternative configurations to that reflected in FIG. 5A.
Figure 5C:
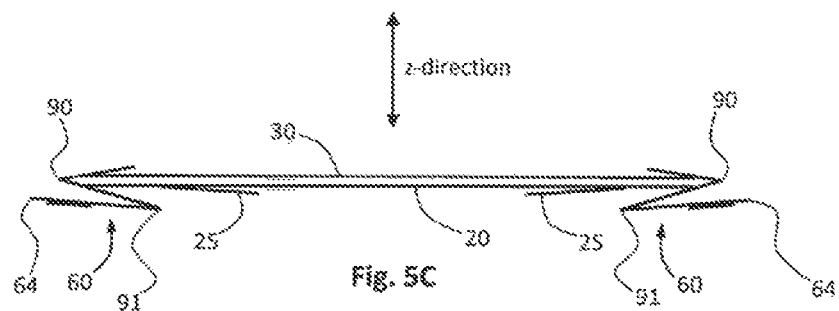

In an alternative to the temporary folding configuration shown FIGS. 3-5A, as reflected in FIG. 5C, each fastening member 60 may be imparted with two longitudinal folds as suggested in FIG. 5A, but rather than being folded to the outside of the diaper, the fastening member may be folded to the inside of the diaper. Each fastening member 60 may be imparted with a first longitudinal fold 90, at which the fastening member 60 is folded forward over itself (and in the example of FIG. 5C, over the wearer-facing side of the diaper), toward the inside in the z-direction. Each fastening member 60 may be imparted with a second longitudinal fold 91 at which the fastening member 60 is again folded over on itself, again toward the inside in the z-direction.

Figure 5D:
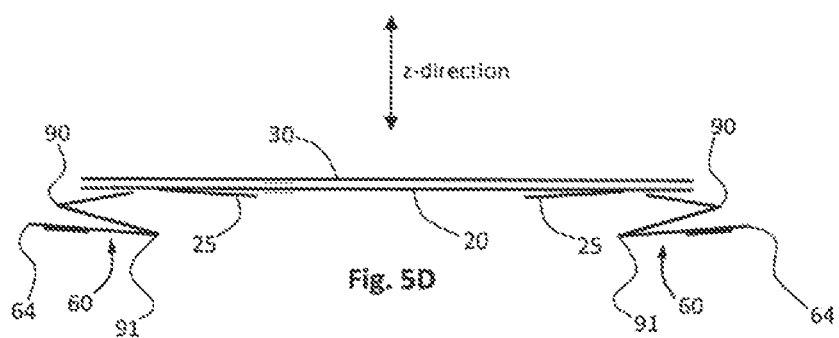

In examples in which the fastening member is attached to the wearer-facing surface such as the topsheet 30, the fastening member may be folded in either of the configurations reflected in FIGS. 5B and 5D.

The temporary fastening member folding configuration reflected in FIGS. 3-5A and 5B may be preferred in some circumstances because it removes the fastening members from proximity to the inner/wearer-facing surfaces of the diaper structure—which may be useful, for example, where inner/wearer-facing surfaces will be subject to processing operations downstream of the fastening member folding operation. On the other hand, where this is not a primary concern, the temporary folding configuration reflected in FIGS. 5C and 5D may be useful, for example, for improved consumer access to the fastening members upon unfolding the diaper, and thus, consumer convenience, or for containing the folded fastening members within the diaper when it is folded along its lateral axis 101 (e.g., as shown FIG. 6) for stacking and packaging as described further below with reference to FIG. 6.

Figure 3:
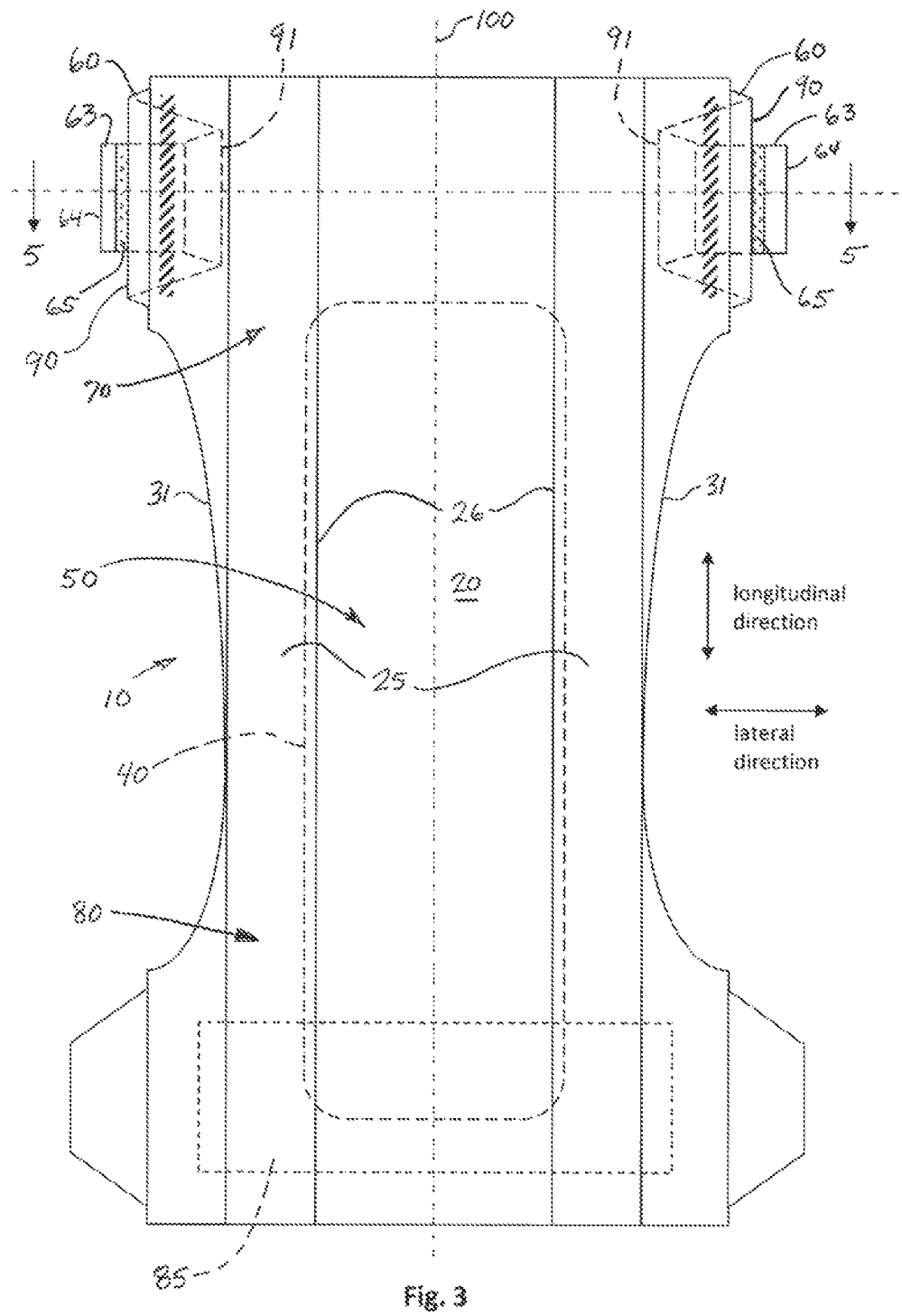
FIG. 3 is a plan view of a disposable diaper shown extended longitudinally and laterally against any contraction induced by included elastic members, with wearer-facing surfaces up and fastening members folded.
Figure 4:
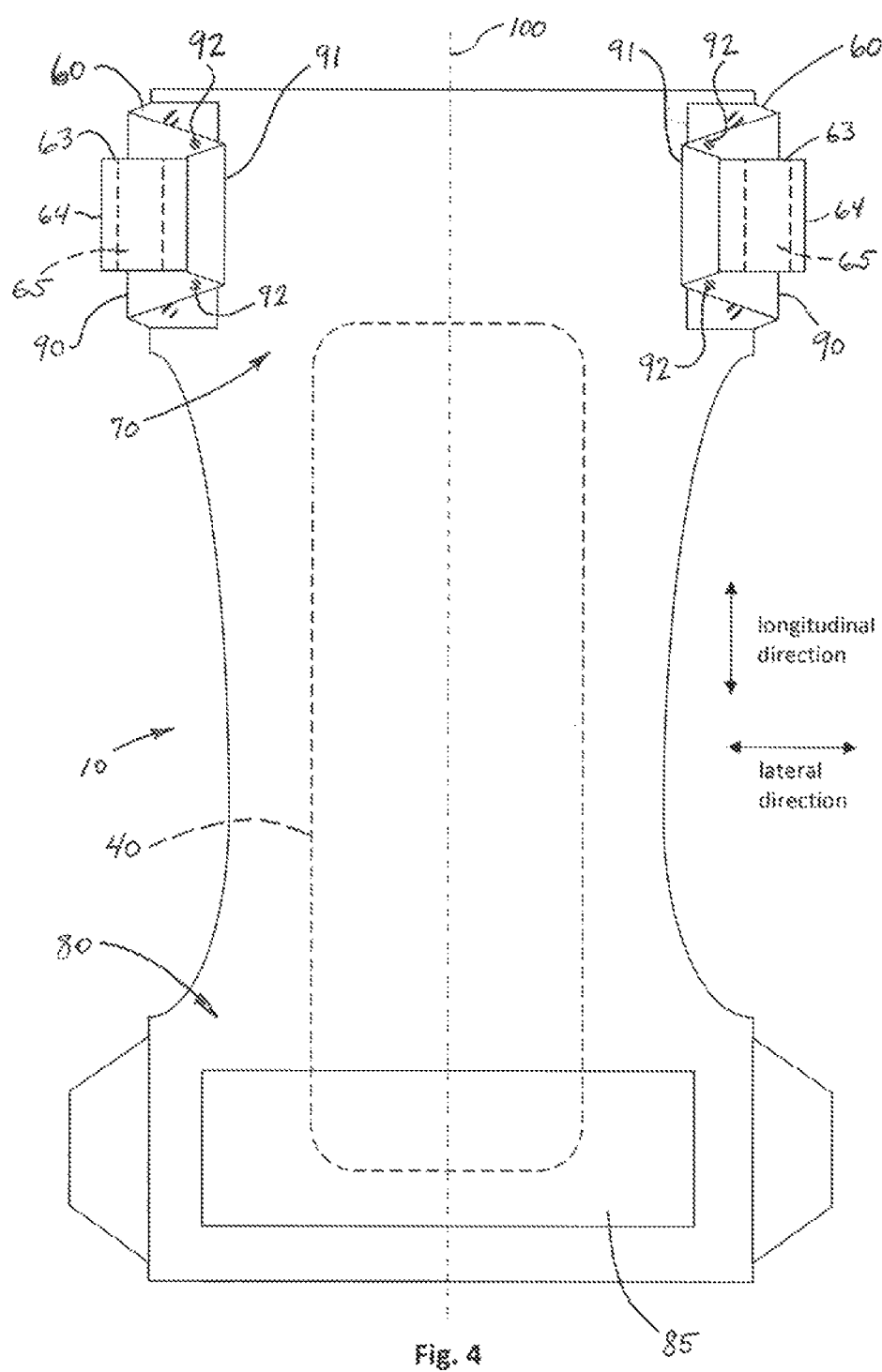
FIG. 4 is a plan view of a disposable diaper shown extended longitudinally and laterally against any contraction induced by included elastic members, with outward facing surfaces up and fastening members folded.

As reflected in the figures, the locations of the first and second longitudinal folds 90, 91 relative the lateral length of the fastening member may be selected such that a distal portion of the graspable end member 63 may be allowed to extend laterally beyond/overhang first longitudinal fold 90. This makes the distal portion of graspable end member 63 readily identifiable and easily graspable by the caregiver with one hand. FIG. 3 reflects a typical position of a diaper (wearer-facing surfaces up) just after it is located beneath a reclining baby; it can be appreciated that with this configuration the caregiver will be able to quickly and easily identify and grasp a distal portion of a graspable end member 63, pull out the folds and extend the fastening member 60 laterally to its fall lateral length, wrap it about the baby's hip, and fasten it to the landing zone (via fastener 65) with one hand (the front portion with the landing zone being held in position on the baby, e.g., by the caregiver with her other hand), in a single motion.

In order to maintain the fastening members in their temporarily folded configuration prior to the time the diaper is to be applied to a baby, the fastening members may be removably attached to themselves by various mechanisms. In a non-limiting example depicted in FIG. 4, the fastening members may be tacked to themselves via one or more tack bonds 92. Tack bonds 92 may be positioned to attach an intermediate portion of the fastening member (i.e., the portion between the folds) to a proximal portion (the portion laterally inward of the first fold 90), or to attach an intermediate portion of the fastening member to a distal portion of the fastening member (the portion extending away from the second fold 91 and ending at distal end 64), or a combination thereof. Alternatively, one or more tack bonds may be positioned to attach an intermediate portion or proximal portion of the fastening member to the diaper chassis, the topsheet, backsheet or a barrier cuff. Tack bonds 92 may be adhesive bonds, thermal bonds or any other suitable bonding mechanism by which attachment between components is effected, but substantially non-destructive detachment thereof may be effected by tugging the fastening member laterally outward. In one non-limiting example, tack bonds may be formed by a frangible bonding agent such as described in U.S. Pat. No. 8,454,571, disposed between the components to be attached to one another. Such a frangible bonding agent may have good adhesive strength when freshly deposited but may lose adhesive strength over time, thereby providing for good holding during manufacturing but providing for easy, nondestructive detachment at the time of consumer use. An example of a frangible bonding agent is PHO-3005 type fugitive hot-melt adhesive available from H. B. Fuller, St. Paul, Minn. In another non-limiting example, a frangible bonding agent may be a material forming a relatively weak bond (i.e., weaker than that formed by typical diaper construction adhesives) such as but not limited to a wax, for example, paraffin wax, microcrystalline wax, synthetic wax, beeswax and other natural waxes, etc.

In a non-limiting example, a tack bond may be effectively created by an appropriate coordination of fastener 65 location with the locations of first and second folds 90, 91. For example, as reflected in FIGS. 3-5, with an appropriate configuration and coordination of these locations all or a portion of fastener 65 may be disposed in facing contact with the intermediate portion of the folded fastening member 60. Where fastener 65 is adapted to attach or adhere to surfaces of the kind of the material forming the fastening member 60, the portion of fastener 65 in facing contact with the intermediate portion can serve to create a tack bond. For example, if fastener 65 is a patch of hooks that will attach to a nonwoven, and fastening member 60 has a wearer-facing layer of nonwoven, fastener 65 will attach to the intermediate portion of the fastening member to form a tack bond thereto. In another example if fastener 65 is a patch or strip bearing adhesive material, fastener 65 may effectively attach to the intermediate portion to form a tack bond thereto, under various combinations of adhesive material and wearer-facing material of the fastening member 60.

Figure 6:
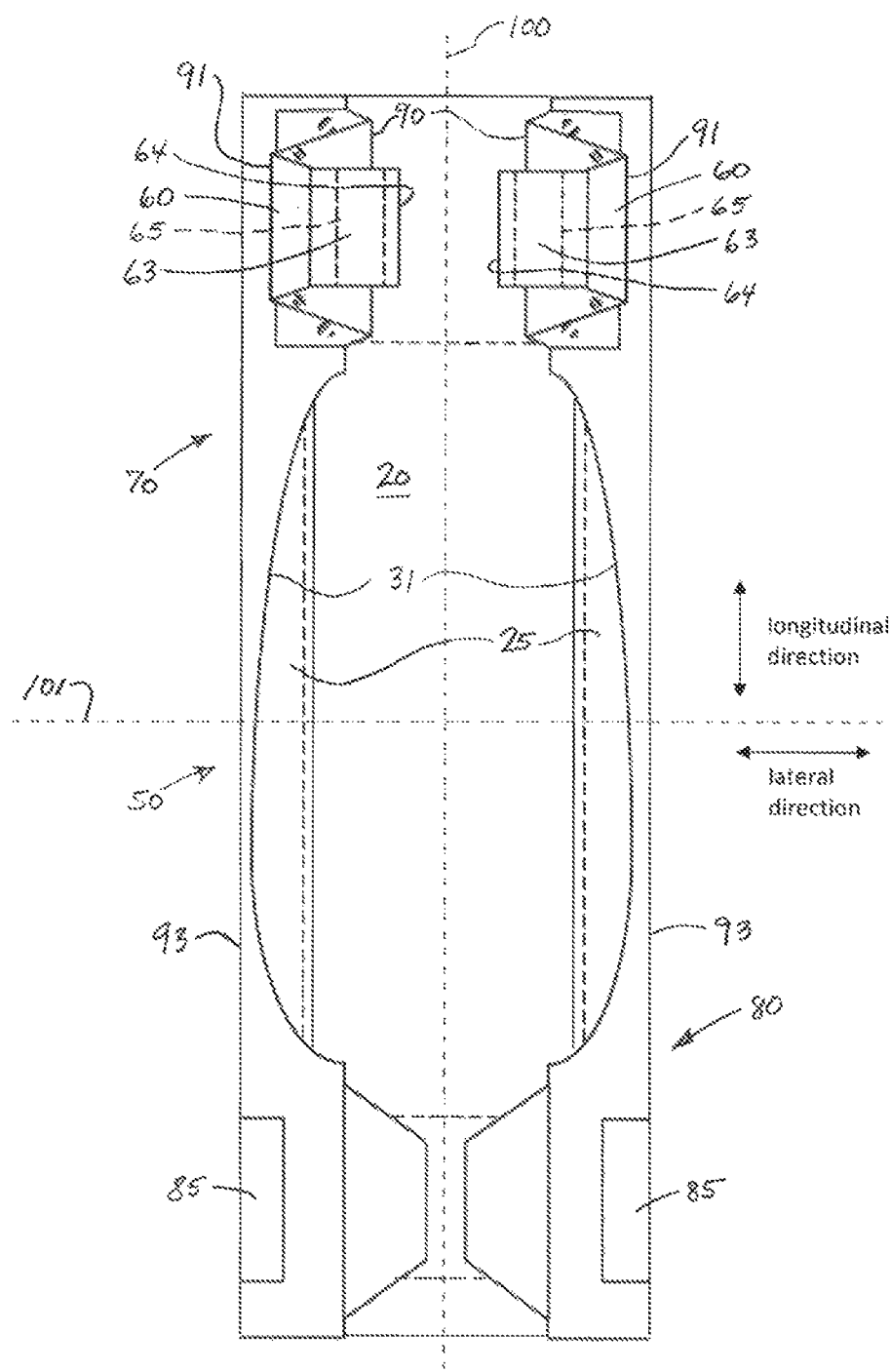
FIG. 6 is a plan view of a disposable diaper shown extended longitudinally and laterally against any contraction induced by included elastic members, with wearer-facing surfaces up, and side portions and fastening members folded.

Disposable diapers are often folded further for packaging. As shown in FIG. 6, a diaper may be imparted with third folds 93 at which larger longitudinal portions of the diaper (which may include portions along the leg edges 31 and portions of the barrier cuffs 25) are folded laterally inward, to consolidate the diaper for stacking and packaging. The diaper may be imparted with a fourth fold along lateral line 101 about which the diaper is folded with wearer-facing surfaces inside, thereby folding its longitudinal length approximately in half, again, for purposes of consolidation for stacking and packaging. Viewing FIG. 6, however, it can be seen that the fastening member folding configuration herein still makes the distal portions of graspable end members 63 readily identifiable, graspable, extendable and fastenable by the caregiver using one hand and a single motion.

Combinations of features including but not limited to the following combinations are contemplated herein:

1. A disposable diaper, comprising:
    a chassis comprising a topsheet; a backsheet; an absorbent core disposed between the topsheet and the backsheet; a front waist region ending at a front lateral waist edge; a rear waist region ending at a rear lateral waist edge; a crotch region between the front waist region and the rear waist region; a longitudinal centerline; a pair of opposing left and right longitudinal edges extending from the front lateral waist edge to the rear lateral waist edge; a landing zone disposed on the backsheet and in the front waist region; and a pair of longitudinal barrier cuffs affixed to the chassis proximate the topsheet; and
    a pair of oppositely-disposed fastening members each attached to the rear waist region at an attachment location, each fastening member having a wearer-facing surface and an outward-facing surface,
    wherein, for each fastening member:
        a proximal portion extends laterally away from the attachment location and the longitudinal centerline to a first longitudinal fold; an intermediate portion extends from the first longitudinal fold laterally toward the longitudinal centerline to a second longitudinal fold; and a distal portion extends from the second longitudinal fold laterally away from the longitudinal centerline, and ends a distal end of the fastening member, and
        the fastening member further comprises a fastener disposed on the wearer-facing surface of the distal portion, the fastener being configured to fastenably engage the landing zone.
2. The disposable diaper of Combination 1 wherein the second longitudinal fold is disposed to the outside of the backsheet in the z-direction.
3. The disposable diaper either of the preceding combinations wherein the fastener is disposed in facing contact with the intermediate portion.
4. The disposable diaper of any of the preceding combinations wherein the distal end of the fastening member lies laterally outside the first longitudinal fold.
5. The disposable diaper of any of the preceding combinations wherein the distal end of the fastening member lies laterally outside a nearest of the left and right longitudinal edges.

6. The disposable diaper of any of the preceding combinations wherein one of the proximal, intermediate or distal portions of each fastening member is tacked to another of the proximal, intermediate or distal portions, or to the topsheet, the backsheet, or the barrier cuffs.

All patents and patent applications (including any patents which issue thereon) referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable diaper, comprising:
    a chassis comprising a topsheet; a backsheet; an absorbent core disposed between the topsheet and the backsheet; a front waist region ending at a front lateral waist edge; a rear waist region ending at a rear lateral waist edge; a crotch region between the front waist region and the rear waist region; a longitudinal centerline; a pair of opposing left and right longitudinal edges extending from the front lateral waist edge to the rear lateral waist edge; a landing zone disposed on the backsheet and in the front waist region; and a pair of longitudinal barrier cuffs affixed to the chassis proximate the topsheet, the diaper having a folded diaper configuration and an extended diaper configuration; and
    a pair of oppositely-disposed fastening members each attached to the rear waist region at an attachment location, each fastening member having a wearer-facing surface and an outward-facing surface, and a folded fastening member configuration and an extended fastening member configuration, associated with the folded diaper configuration and an extended diaper configuration, respectively,
    wherein, for the folded diaper configuration and each fastening member in the folded fastening member configuration:
        a proximal portion of the fastening member extends laterally away from the attachment location and toward the longitudinal centerline to a first longitudinal fold; an intermediate portion of the fastening member extends from the first longitudinal fold laterally away from the longitudinal centerline to a second longitudinal fold; and a distal portion of the fastening member extends from the second longitudinal fold laterally toward the longitudinal centerline, and ends at a distal end of the fastening member;
        a portion of the chassis in the rear waist region including the attachment location is folded laterally inwardly along a third longitudinal fold proximate one of the longitudinal edges, toward the longitudinal centerline;
        the fastening member further comprises a fastener disposed on the wearer-facing surface of the distal portion, the fastener being configured to fastenably engage the landing zone;
        the second longitudinal fold is disposed to the inside of the backsheet along a z-direction; and
        in the folded diaper configuration, the distal end of the fastening member lies laterally to the inside of the first longitudinal fold.

2. The disposable diaper of claim 1 wherein the distal end of the fastening member lies laterally to the inside of a nearest of the left and right longitudinal edges when the diaper is in the folded diaper configuration.

3. The disposable diaper of claim 1 wherein one of the proximal, intermediate or distal portions of each fastening member is tacked to another of the proximal, intermediate or distal portions, or to the topsheet, the backsheet, or the barrier cuffs.

* * * * *